United States Patent [19]

Abrahmsén et al.

[11] Patent Number: 5,143,844
[45] Date of Patent: Sep. 1, 1992

[54] CONSTRUCTION OF AN IGG BINDING PROTEIN TO FACILITATE DOWNSTREAM PROCESSING USING PROTEIN ENGINEERING

[75] Inventors: Lars Abrahmsén, Stockholm; Tomas Moks, Täby; Björn Nilsson, Sollentüna; Mathias Uhlën, Upsala, all of Sweden

[73] Assignee: KabiGen AB, Stockholm, Sweden

[21] Appl. No.: 594,564

[22] Filed: Oct. 9, 1990

[30] Foreign Application Priority Data

Dec. 13, 1985 [SE] Sweden .................................. 8505922

[51] Int. Cl.$^5$ ...................... C12N 15/31; C12N 15/62; C12N 15/63
[52] U.S. Cl. ................................ 435/257.3; 435/69.7; 435/370.1; 530/417
[58] Field of Search ................ 435/69.7, 172.3, 252.3, 435/320.1; 530/412

[56] References Cited

U.S. PATENT DOCUMENTS 4,769,326  9/1988  Rutter ............................... 435/69.7

FOREIGN PATENT DOCUMENTS

WO8403103  8/1984  PCT Int'l Appl. .

OTHER PUBLICATIONS

J. Biol. Chem. 259;1695–1702, Feb. 10, 1984, Uhlen et al., Complete Sequence of the Staplylococcal Gene Encoding Protein A.
P.N.A.S. 82:7646–7650, Nov. 1985, Whitney et al. Detection of Neutral Amino Acid Substitutions in Proteins.

*Primary Examiner*—David L. Lacey
*Assistant Examiner*—John D. Ulm
*Attorney, Agent, or Firm*—Burns, Doane, Swecker, & Mathis

[57] ABSTRACT

A recombinant DNA fragment (Z) coding for an immunoglobulin G binding domain related to staphylococcal protein A. The methionine codon of the recombinant DNA fragment has been replaced with a codon of an amino acid residue other than methionine to enable expression of a methionine-free protein. The present invention is also directed to recombinant DNA sequence containing such recombinant DNAS fragment (Z) as well as a recombinant DNA molecule, plasmid vector and bacterial cell containing such recombinant DNAS fragment. Also disclosed is a process for cleaving a fused protein expressed in a biological system using said recombinant DNA fragment.

30 Claims, 7 Drawing Sheets

Fig. 1

| S | E | D | A | B | C | X |

Fig. 2

```
         ADNKFNKE QQNAFYEIL NMPNLNE EQRNGFIQSLKD DPSQSANVLAEAKKLNDSQAPK
         1         10        20       30           40        50

E    AQHDEA ----+-QV- ----+-A D----+-----  +---+----G--Q++-+-+--
D    ---+N---D --S+----+  +------ A-+++-+-+-+  ----T---G---+++E---+-
A    ---N----  ------+  -------  -------+--  ---+--L+S----+-E---+-
B    --------  ------  HL----  ----+--  ------L---------A----
C    -+------  ------+- HL---T-  --+++------+ +++V-KEI-------+-A----
```

Fig. 3

Z-fragment                   226 BASES

```
  1HindIII    11         21 FspI    31           41AccI    51
AAGCTTCCGCGGCAAATGCTGCGCAACACGATGAAGCCGTAGACAACAAATTCAACAAA
                         AlaGlnHisAspGluAla ValAspAsnLysPheAsnLys
                         └──Cleavage         └──Z-region
                            region 60        70        80        90        100       110
GAACAACAAAACGCGTTCTATGAGATCTTACATTTACCTAACTTAAACGAAGAACAACGA
GluGlnGlnAsnAlaPheTyrGluIleLeuHisLeuProAsnLeuAsnGluGluGlnArg 120       130       140       150       160       170
AACGCCTTCATCCAAAGTTTAAAAGATGACCCAAGCCAAAGCGCTAACCTTTTAGCAGAA
AsnAlaPheIleGlnSerLeuLysAspAspProSerGlnSerAlaAsnLeuLeuAlaGlu 180       190       200       210AccI  220EcoRI
GCTAAAAAGCTAAATGATGCTCAGGCGCCGAAAGTAGACGCGAATTC
AlaLysLysLeuAsnAspAlaGlnAlaProLysValAspAlaAsn
```

Fig. 4

ZZ-IGF-1　　　　　　　　　　894 BASES

```
1         11        21        31        41        51
TCGAAATAGCGTGATTTTGCGGTTTTAAGCCTTTTACTTCCTGAATAAATCTTTCAGCAA 61        71        81        91        101       111
AATATTTATTTTATAAGTTGTAAAACTTACCTTTAAATTTAATTATAAATATAGATTTTA 121       131       141       151       161       171
GTATTGCAATACATAATTCGTTATATTATGATGACTTTACAAATACATACAGGGGGTATT 181       191       201       211       221       231
AATTTGAAAAAGAAAAACATTTATTCAATTCGTAAACTAGGTGTAGGTATTGCATCTGTA
   LeuLysLysLysAsnIleTyrSerIleArgLysLeuGlyValGlyIleAlaSerVal 241       251       261       271       281       291
ACTTTAGGTACATTACTTATATCTGGTGGCGTAACACCTGCTGCAAATGCTGCGCAACAC
ThrLeuGlyThrLeuLeuIleSerGlyGlyValThrProAlaAlaAsnAlaAlaGlnHis
                              The signal sequence     Cleavage
301       311  AccI 321       331       341       351   region
GATGAAGCCGTAGACAACAAATTCAACAAAGAACAACAAAACGCGTTCTATGAGATCTTA
AspGluAlaValAspAsnLysPheAsnLysGluGlnGlnAsnAlaPheTyrGluIleLeu
              Z-region 361       371       381       391       401       411
CATTTACCTAACTTAAACGAAGAACAACGAAACGCCTTCATCCAAAGTTTAAAAGATGAC
HisLeuProAsnLeuAsnGluGluGlnArgAsnAlaPheIleGlnSerLeuLysAspAsp 421       431       441       451       461       471
CCAAGCCAAAGCGCTAACCTTTTAGCAGAAGCTAAAAAGCTAAATGATGCTCAGGCGCCG
ProSerGlnSerAlaAsnLeuLeuAlaGluAlaLysLysLeuAsnAspAlaGlnAlaPro 481 AccI  491       501       511       521       531
AAAGTAGACAACAAATTCAACAAAGAACAACAAAACGCGTTCTATGAGATCTTACATTTA
LysValAspAsnLysPheAsnLysGluGlnGlnAsnAlaPheTyrGluIleLeuHisLeu
              Z-region 541       551       561       571       581       591
CCTAACTTAAACGAAGAACAACGAAACGCCTTCATCCAAAGTTTAAAAGATGACCCAAGC
ProAsnLeuAsnGluGluGlnArgAsnAlaPheIleGlnSerLeuLysAspAspProSer 601       611       621       631       641       651
CAAAGCGCTAACCTTTTAGCAGAAGCTAAAAAGCTAAATGATGCTCAGGCGCCGAAAGTA
GlnSerAlaAsnLeuLeuAlaGluAlaLysLysLeuAsnAspAlaGlnAlaProLysVal 661  EcoR671      681       691       701       711
GACGCGAATTCTAACGGTCCCGAAACTCTGTGCGGTGCTGAACTGGTTGACGCTCTGCAG
AspAlaAsnSerAsnGlyProGluThrLeuCysGlyAlaGluLeuValAspAlaLeuGln
                                  IGF-1
721       731       741       751       761       771
TTTGTTTGCGGTGACCGTGGTTTTTATTTTAACAAACCCACTGGTTATGGTTCTTCTTCT
PheValCysGlyAspArgGlyPheTyrPheAsnLysProThrGlyTyrGlySerSerSer 781       791       801       811       821       831
CGTCGTGCTCCCCAGACTGGTATTGTTGACGAATGCTGCTTTCGTTCTTGCGACCTGCGT
ArgArgAlaProGlnThrGlyIleValAspGluCysCysPheArgSerCysAspLeuArg 841       851       861       871       881      891HindIII
CGTCTGGAAATGTATTGCGCTCCCCTGAAACCCGCTAAATCTGCTTAGAAGCTT
ArgLeuGluMetTyrCysAlaProLeuLysProAlaLysSerAla***
```

CONSTRUCTION OF AN IGG BINDING PROTEIN TO FACILITATE DOWNSTREAM PROCESSING USING PROTEIN ENGINEERING

This application is a continuation of application Ser. No. 941,179, filed Dec. 12, 1986, now abandoned.

The present invention relates to a recombinant DNA fragment coding for an immunoglobulin G (hereinafter called IgG) binding domain related to staphylococcal protein A, to DNA sequences comprising such fragments and to a process for cleavage of a fused protein expressed by using such fragment or sequence. The invention also relates to plasmid vectors and bacterial cells harboring such recombinant DNA fragments or sequences. Basically, the present invention relates to an improved system for producing and purifying foreign proteins expressed in bacteria.

Gene fusion techniques have been used in recombinant DNA technology to monitor the transient expression from a gene or to facilitate the downstream processing. By making a gene fusion to staphylococcal protein A any gene product can be purified as a fusion protein to protein A and can thus be purified in a single step using IgG affinity chromatography. We have earlier fused the protein A gene to a synthetic gene encoding human insulin-like Growth Factor I (IGF-I). The hybrid protein expressed could be recovered in high yield from the growth medium of *Staphylococcus aureus*. We have also shown that a gene product consisting of divalent protein A fused to IGF-I (EE-IGF-I) was secreted from the *E. coli* cell by a method described in our Swedish patent application (the disclosure of which is incorporated herein by reference; filed simultaneously herewith).

These two mentioned expression systems constitute quite powerful tools for expressing and secreting foreign proteins. The use of protein A fusions, however, is dependent on processing after purification to release a biologically active peptide or protein. In an industrial process chemical cleavage methods are preferred compared to proteolytic cleavages for economic reasons. When using protein A as the carrier protein it would be advantageous if the recognition amino acid sequence would be present only in the linker to be processed to release the attached gene product so that the protein A portion could be left intact. In that way a second passage through an IgG column would bind the protein A molecule, but the product released by the chemical cleavage would pass through.

For IGF-I the method suggested by us to be used is hydroxylamine cleavage in Asn-Gly dipeptide sequences. The method mostly used is otherwise CNBr cleavage specific for Met. The choice of method is dependent on if the amino acid(s) sensitive for the chemical is present in the product or not. IGF-I has an internal methionine and IGF-II does not. Protein A has, however, 3 internal methionines in the IgG binding region and 5 Asn-Gly in the IgG binding region of protein A. This makes the second passage through the column irrelevant as the protein A pieces released from the cleavage will not bind to the IgG.

The main object of this invention is to provide a solution to these problems by adapting an IgG binding domain so that no Met and optionally no Asn-Gly is present in the sequence. At the same time two non-palindronic AccI sites are preferably introduced in the fragment to be able to polymerize the IgG binding domain to any number of IgG binding domains.

Accordingly, for attaining said object and other objects which will be clear from the following disclosure, the invention provides for a recombinant DNA fragment (abbreviated Z in this disclosure) coding for an immunoglobulin G binding domain related to staphylococcal protein A, such fragment being characterized in that the methionine codon of said fragment has been replaced by a codon of another amino acid residue enabling expression of a methionine-free protein. It is preferred that the codon of said other amino acid residue is that of leucine.

In a preferred embodiment of the fragment of the invention the asparagine-methionine codons have been replaced by histidine-leucine codons. The codon of amino acid residue No. 1 as defined by trypsin digestion of native protein A is preferably replaced by a valine codon, so as to give at the nucleotide level the sequence GTAGAC furnishing a non-palindromic Acc I site.

In another preferred embodiment, the glycine codon in the Asn-Gly constellation has been replaced by an alanine codon. The Asp-Pro codons have suitably been modified to increase the acid stability of the peptide bond of the expressed protein, for example by replacing the aspartic acid codon with a glutamic acid codon.

According to another aspect of the invention there is provided for a recombinant DNA sequence comprising at least two Z-fragments as defined above. The number of such amalgamated Z-fragments is preferably within the range 2–15, and particularly within the range 2–10.

According to still another aspect of the invention there is provided for a recombinant DNA fragment coding for any of the E D A B C domains of staphylococcal protein A, wherein the glycine codon(s) in the Asn-Gly coding constellation has been replaced by an alanine codon.

The invention also provides for a recombinant DNA sequence comprising the Z-fragment as defined above preceded by a signal sequence followed by a nucleotide sequence coding for the amino acid sequence: Ala Gln His Asp Glu Ala.

The invention also covers a recombinant DNA molecule comprising the recombinant DNA sequence as described above and fused at the 3′ end thereof at DNA level, a production gene. By this arrangement such molecule obtains the ability to express a fused protein in a suitable host. Such production gene may be that of a somatomedin, examples of which are: growth hormones or factors, such as hGH (human growth hormone), IGF-I, IGF-II, NGF (Nerve Growth Factor), EGF (Epithermal Growth Factor) and PDGF (Platelet Derived Growth Factor). The production gene may also be one coding for an interferon, interleukin-2, insulin, neuropeptide, gastrointestinal peptide etc. Specifically, the production gene is that of IGF-I or IGF-II. The production gene may also code for a structural gene for an enzyme or parts thereof.

It is preferred that in such recombinant DNA molecule the N-terminal glycine codon is preceded by an asparagine codon to enable hydroxyl amino cleavage of the peptide bond to release the native protein, such as IGF-I. In another embodiment the N-terminal codon is preceded by a methionine codon to enable cyanogen bromide cleavage of the peptide bond to release native protein, such as IGF-II.

According to still another aspect of the invention there is provided a process for cleaving a fused protein expressed in a biological system by the recombinant DNA molecule as defined above. Such treatment is suitably performed by hydroxyl amine treatment when the N-terminal glycine codon is preceded by an asparagine codon. When preceded by a methionine codon the cleavage is preferably performed by cyanogen bromide treatment.

Finally, the invention covers a plasmid vector comprising the recombinant DNA molecule as described above. The invention also extends to bacterial cells harboring the recombinant DNA-molecule defined above. The molecule can be harbored in the chromosome of the bacterial cell but may also be contained in a plasmid vector.

The host cell is for example Gram negative and is particularly constituted by an E. coli.

The invention will in the following be further illustrated by non-limiting examples with reference to the appended drawings, wherein:

FIG. 4 shows the nucleotide sequence of the ZZ-IGF-I encoded by the pZZ-IGF-I plasmid vector. The regions encoding the signal peptide, the cleavage region, the two Z-regions and IGF-I are shown as well as restriction sites relevant for the construction strategy;

Figure 1:
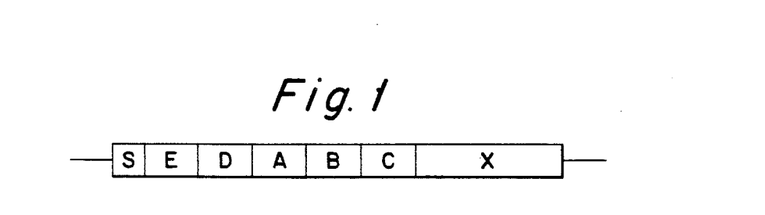
FIG. 1 shows the organization of the coding region of the protein A gene. S is the signal sequence, A–E are the IgG binding domains and X is the C-terminal region with no IgG binding activity of the encoding polypeptide.

By cleaving the cloned synthetic fragment using the restriction enzyme AccI followed by religation of the isolated fragment, the fragments will ligate head to tail and create a tandem repeat of fragment and in theory any number of regions can be obtained. The fragment used to illustrate the invention was constructed in the following way:

Protein A consists of two distinct regions: The IgG binding region (A–E domains) and region X having no IgG binding activity (FIG. 1). The IgG binding region consists of five homologous IgG binding domains which can be cleaved apart by trypsin treatment at the protein level. The B-domain has been crystallized together with IgG and the structure determined by X-ray crystallography (Deisenhofer, J., Biochemistry. 20, 2361 (1981).

Figure 2:
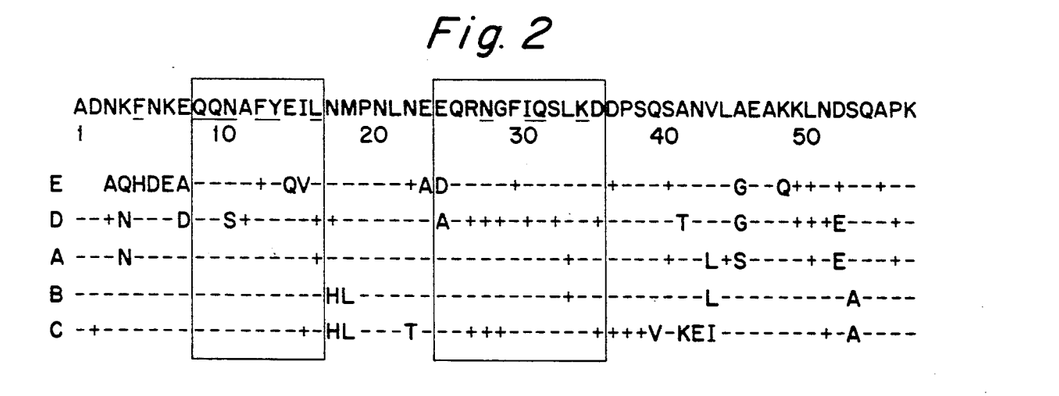
FIG. 2 shows a comparison of the different IgG binding regions. The first line shows a suggested consensus amino acid sequence of the IgG binding regions. The boxes show the stretches of amino acids involved in the two different alpha helixes. The amino acids involved in the binding to IgG are underlined. The amino acids in the different regions are shown by —for no change compared to the consensus codon, +for no amino acid change but a silent mutation and the letter for another amino acid for amino acid changes. The amino acids are given in the one letter code.

The five IgG binding domains consist of approximately 58 amino acids (E is shorter and D is longer) and the amino acid sequences of the regions are shown in FIG. 2.

The fragment that was synthesized had the following features:
1) Lack of any Met;
2) Lack of Asn-Gly dipeptide sequence;
3) The fragment is optimized to be synthesized at the nucleotide level to facilitate cloning to get expression;
4) The fragment can be polymerized at the nucleotide level to get any number of IgG binding regions;
5) The fragment is capable of being expressed in a genetic system adapted for expression and secretion.

1) There are altogether 3 Met in the IgG binding region of protein A. In the synthetic fragment the consensus Met (the protein A consensus amino acid sequence is shown in FIG. 2) was changed in the synthetic fragment by changing the Asn-Met to codons for a His-Leu sequence.

2) The Asn-Gly dipeptide sequence is sensitive to hydroxylamine. As this sequence is kept intact in all five IgG binding domains of protein A and as this amino acid sequence is present in the middle of an alpha helix involved in the binding to IgG (FIG. 2) there is very little chance to be successful in any amino acid change. The obvious choice to change the Asn to a Gln was analyzed by computer graphics (FRODO software, Alwin Jones, Biomedical Centre, Uppsala, Sweden) using the coordinates available from the Brookhaven Protein Data Bank (Bernstein, F.C. et al J.Mol.Biol., 112, 553-542 (1972) calculated from the X-ray crystallographic structure of protein A.

Since the Asn provides for hydrogen bonds to two other residues, the change of the code for the Asn to Gln was expected to destroy both the tertiary structure of protein A and the binding to IgG. Instead, however, the computer analysis surprisingly showed that the Gly in the Asn-Gly dipeptide sequence could be changed to an Ala. This change was not obvious as glycines are among the most conserved amino acids between homologous protein sequences due to their special features. Their features include flexibility around the peptide bond, their usual function is to start and break alpha and beta structures and they feature as an amino acid having no net charge in the polypeptide chain. However, by simulating the Gly to Ala amino acid change in the computer we concluded that this change would not interfere with folding to protein A or binding to IgG.

3) The fragment was synthesized at the at DNA level in 10 separate oligomers. To facilitate cloning of the fragment one HindIII site was designed in the 5′ end and an EcoRI site in the 3′ end. (The nucleotide sequence of the fragment is shown in FIG. 3).

4) In order to be able to polymerize the fragment at the nucleotide level, a non-palindromic AccI site was introduced by changing the nucleotide sequence to GTAGAC in the code for the N-terminal end of the IgG binding region. In that way an Ala codon present in all regions is changed to a Val. By this nucleotide constellation, the fragment can be polymerized to any multiplicity thus altering the binding capacity of the translated product. It is not obvious if this amino acid substitution will interfere with the protein A function or not.

5) By introducing a FspI site where the signal sequence shall be attached to the fragment and by starting the coded fragment with the six amino acids unique for the E-region of protein A the fragment is capable of being attached to the protein A signal sequence by molecular cloning and the six N-terminal amino acids were introduced to ensure secretion of the fragment.

Specific embodiments of the invention will now be described in detail.

STARTING MATERIALS

Bacterial Hosts

Three different strains of *E. coli* K12 were used in the Examples: HB101 (Boyer, H. W. et al J.Mol.Biol., 41, 459–572 (1969), JM 83 (Yanisch-Perron, C. et al Gene, 33, 103–119 (1985)) and JM 103 (Messing, J. et al Methods Enzymol., 101, 20–79 (1983)). (The strains are available at the Dept of Biochemistry and Biotechnology, Royal Insitute of Technology, Stockholm, Sweden.

Cloning Vehicles

The cloning vehicles used in the Examples were M13 mp 18 (Yanisch-Perron, C. et al Gene, 33, 103–119 (1985)) and pUC8 (Vieva, J. et al Gene 19, 259 (1982)). The vector pHL33 is a vector derived from pEMBL19 (−) (Dente et al, Nucl.Acids Res., 11, 1645 (1983)) and pRIT4 (Nilsson, B. et al, EMBO J. 4, 1075 (1985)) constructed in the following way:

The plasmid pRIT4 was cleaved with Taq I and after fill-in reaction with Klenow polymerase, Not-I linkers were added. The reaction mixture was cleaved with EcoRI Not I and the fragment spanning over the protein A gene was isolated. This fragment was cloned into pEMBL19 (−), where the ClaI site previously had been linked to a NotI site, by cleaving that plasmid with NotI and EcoRI. This gives a vector containing a part of the protein A gene followed by the mp19 multirestriction enzyme linker.

The vector pEX4-IGF-I is pEX (Stanley, K. et al EMBO J. 3, 1429 (1984) having the synthetic IGF-I cloned in EcoRI to BamHI′.

The synthetic gene encoding IGF-I has been described by Elmblad, A. et al in Third European Congress on Biotechnology III, 287–296, Verlag Chemie, Weinheim (1984). The plasmid vector pASZ2 has been deposited with the Deutsche Sammlung von Mikroorganismen (DSM), Göttingen, Federal Republic of Germany, under No. 3594 DSM and (the designated name pE*2 in the deposition document).

BUFFERS AND MEDIA

Coating Buffer 1.59 g $Na_2CO_3$, 2.93 g $NaHCO_3$ and 0.2 g $NaN_3$, made up to 1 liter with distilled $H_2O$

PBST 8.0 g NaCl, 0.2 g $KH_2PO_4$, 2.9 g $Na_2HPO_4 \times 12H_2O$, 0.2 g KCL, 0.2 ml Tween ® 20 and 0.2 g $NaN_3$ made up to 1 liter with distilled $H_2O$ (pH 7.4).

TSB 30 g Tryptic Soy Broth, made up to 1 liter and autoclaved.

LB 10 g Bacto tryptone, 5 g Yeast extract and 10 g NaCl made up to 1 liter and autoclaved.

LA

Plates containing LB and 15 g Bacto Agar per liter.

TBAB 30 g Tryptic Blood Agar Base, made up to 1 liter and autoclaved.

ONPG-buffer 2 mM o-Nitrophenyl-β-D-galactoside (ONPG, Sigma product No N-1127) in 0.1M potassium phosphate buffer, pH 7.3, containing 15 mM 2-mercaptoethanol and 1 mM $MgCl_2$.

Routine Methods

Certain procedures were carried out repeatedly in the Examples. Unless otherwise specified, they were done exactly as follows each time they were carried out.

Methods used routinely in molecular biology are not described (like the use of commercial restriction enzymes, DNA-ligations, Bal 31 exonuclease, S1 nuclease and Klenow polymerase)

Transformations

Transformation of *E. coli* K12 with plasmid DNA was performed exactly as described (Morrison, D. A., Methods in Enzymology, Academic Press 68, 326–331 (1979)). The transformants were selected in a conventional manner on plates (TBAB) containing 70 mg/l ampicillin.

Isolation of Plasmid DNA

Plasmid DNA was isolated as described by Birnboim, H. C. et al, Nucl. Acids Res. 7, 1513 (1979). Small scale preparations to screen a large number of transformants were made exactly as described by Kieser, T. Plasmid 12, 19-36 (1984).

Sepharose 6B Chromatography

Plasmid DNA to be used for Bal31 or S1 treatment were run on a Sepharose 6B gelfiltration in a 10 mM Tris, 1 mM EDTA and 500 mM NaCl-buffer. In this way DNA is separated from RNA.

Elution of DNA Fragments

Elution of DNA fragments from either agarose or polyacrylamide gel pieces were performed exactly as described by Maxam et al, P.N.A.S. (USA), 74, 560-564 (1977).

Ligation of DNA in Low Gel Temperature Agarose Gel

Ligation directly in agarose gel was performed by running the electrophoresis in a Low Gel Temperature Agarose gel and after cutting out the band, the gel piece was melted by heating to 65° C. After a 10 fold dilution using Tris buffer (10 mM pH 7.4) ligation could be performed.

Detection and Quantification of Protein A

An ELISA test (Enzyme linked immunosorbent assay) was used to quantify protein A. The test makes use of a special microtiter plate (Titertek, Amstelstad, Netherlands) having no net charge. The wells are coated with human IgG (Kabi AB, Sweden) in a coating buffer. Test samples are added and protein A is bound to the Fc portions of the IgG adsorbed in the well. Protein A is then assayed by an anti-protein A (from rabbit) conjugated to $\beta$-galactosidase (from Pharmacia AB, Uppsala, Sweden).

Assay

The wells of a microtiter plate are filled with 75 $\mu$l of a solution of human IgG at 16 ng/ml in Coating Buffer and the plate is incubated at room temperature for at least 1 hour. The wells are washed three times with 100 $\mu$l PBST and 50 $\mu$l of sample is added to each well. For quantitative determination 2 fold dilutions are made. After incubation for 1 hour the wells are washed 3 times with 100 $\mu$l PBST followed by addition of 50 $\mu$l anti-protein A-$\beta$-galactosidase (the amount of protein A binding capacity added to each well corresponds to the molar amount of IgG added to each well as detected by titration with protein A in excess). After incubation for 45 minutes, the wells were washed 3 times with 100 $\mu$l PBST followed by addition of 125 $\mu$l ONPG buffer. After incubation for 20-30 minutes 150 $\mu$l 0.1M NaOH was added to stop the reaction. The quantification is made by running a 2-fold dilution of a protein A standard solution of known concentration in parallel with the 2-fold dilutions of the test samples. The absorbance at 405 nm is measured for each well by a photometer.

SDS-PAGE

SDS-polyacrylamide gel electrophoresis was performed exactly as described by Laemmli, O.K. Nature (London), 227, 680-685 (1970) using a 10-20% step gradient gel.

EXAMPLES

I Construction of a Synthetic Protein A Fragment (Z)

The derived DNA sequence was analyzed by a computer program and divided into 10 oligonucleotides varying in length from 41 to 45 nucleotides and with an overlap of 6 bp.

Synthesis was effected on a fully automated machine and the deprotected oligomers were purified by polyacrylamid electrophoresis (20% polyacrylamide, 7M Urea, 50 mM Tris-borate pH 8.3) followed by extraction into water and lyophilization.

II Ligation and Cloning of Z-Fragment 100 pmoles of oligonucleotides A1-A5 and B1-B5 were phosphorylated separately in 20 $\mu$l Kinase buffer (50 mM Tris-HCl pH 7.6, 10 mM MgCl$_2$, 1 mM ATP. 10 mM DTT) 5 units of polynucleotide kinase was added and the mixtures were incubated for 45 minutes at 37° C.

5 $\mu$g of the vector M13mp18, replicative form, was digested with the restriction enzymes EcoRI and HindIII. The large fragment from the digestion was isolated from a low temperature agarose gel.

The agarose containing digested M13 mp18 was melted at 65° C. and 5 $\mu$l (0.5 $\mu$l, 0.1 p mole) was mixed with 0.5 p mole each of the phosphorylated oligomers A1-A5 and B1-B5 in 50 $\mu$l ligation buffer (66 mM Tris-HCl pH 7.6 50 mM MgCl$_2$, 50 mM DTT, 1 mM ATP) heated to 90° C. and slowly cooled to room temperature during one hour. 10 units of T4 DNA ligase was added and the mixture was incubated overnight at 15° C.

E. coli JM 103 was transfected with the DNA thus obtained and grown overnight on 2$\times$YT plates containing x-gal and IPTG. 78 white plaques were transferred to a new 2$\times$YT plate and grown as colonies. Colony hybridization with $^{32}$P labelled oligonucleotide B5 as probe gave one positive colony which was picked and grown in 15 ml 2$\times$YT with E. coli JM 103. The cells were spun down and the phages were recovered from the supernatant. The single stranded phage DNA was extracted and purified and was used as template for the sequencing reaction according to the dideoxy method. The M13mp18 containing the Z-fragment was designated M13-Z.

III Construction of the Plasmid Vector pASZ2

Figure 7:
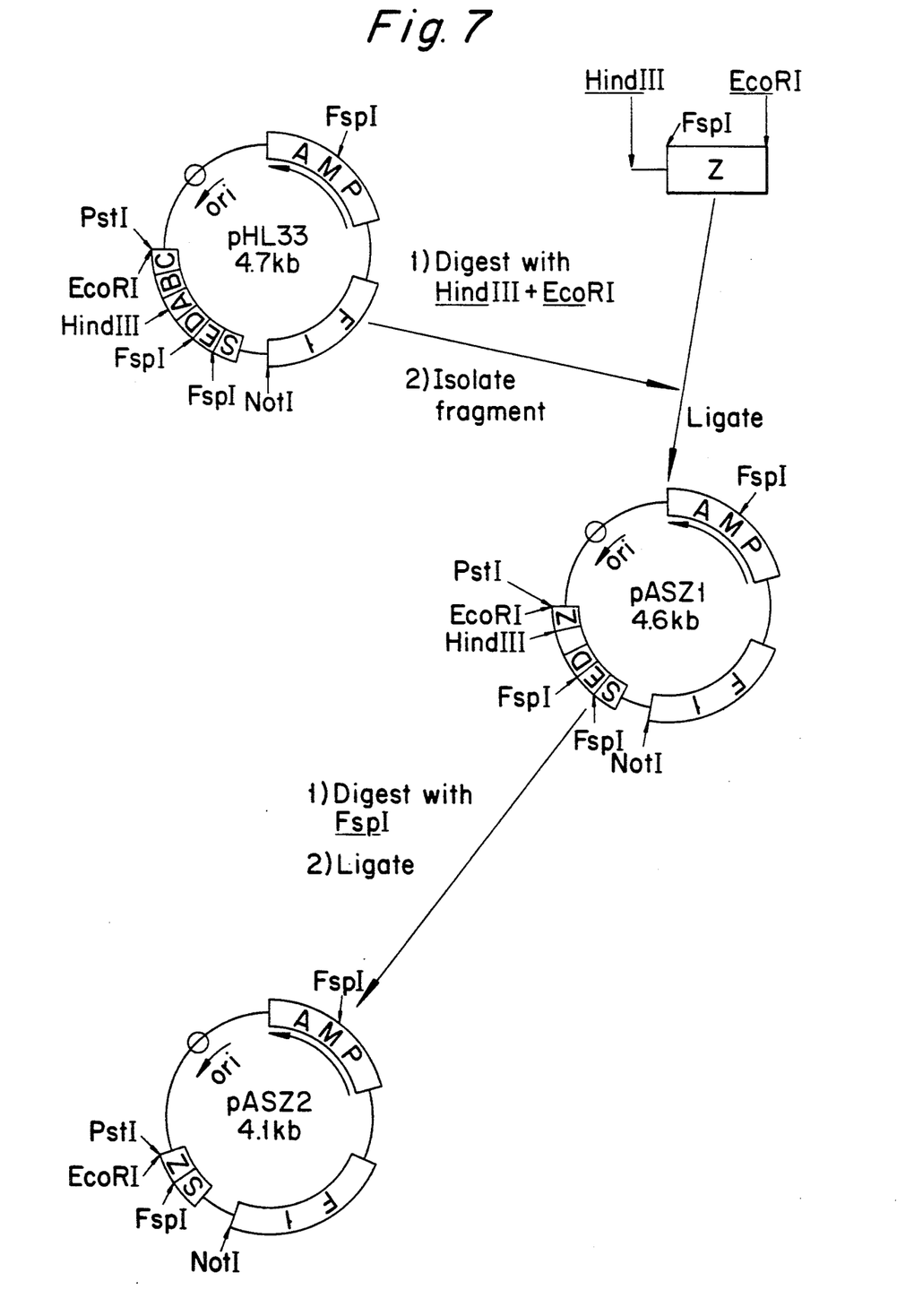
FIG. 7 shows the construction of pASZ1 and pASZ2 as, described in Examples sections III and IV. AMP is the gene encoding the β-lactamase, F1 is the origin of replication for phage f1, S is the signal sequence, A–E are the IgG binding regions, ori is the origin of replication for E.coli and Z is the synthetic fragment.

The plasmid vector PHL33 was cleaved with HindIII and EcoRI. The large fragment was isolated from a 1% agarose gel after electrophoresis. The fragment was ligated to an isolated Z-fragment (HindIII/EcoRI). After ligation the mixture was transformed to E. coli HB101 and the isolated vector PASZ1 (FIG. 7) has the synthetic Z-fragment cloned down stream from the signal sequence. In order to place the synthetic fragment directly after the signal sequence the pASZ1 vector was cleaved with FspI. After religation the mixture was transformed into E. coli HB101 and pASZ2 could be isolated.

Figure 3:
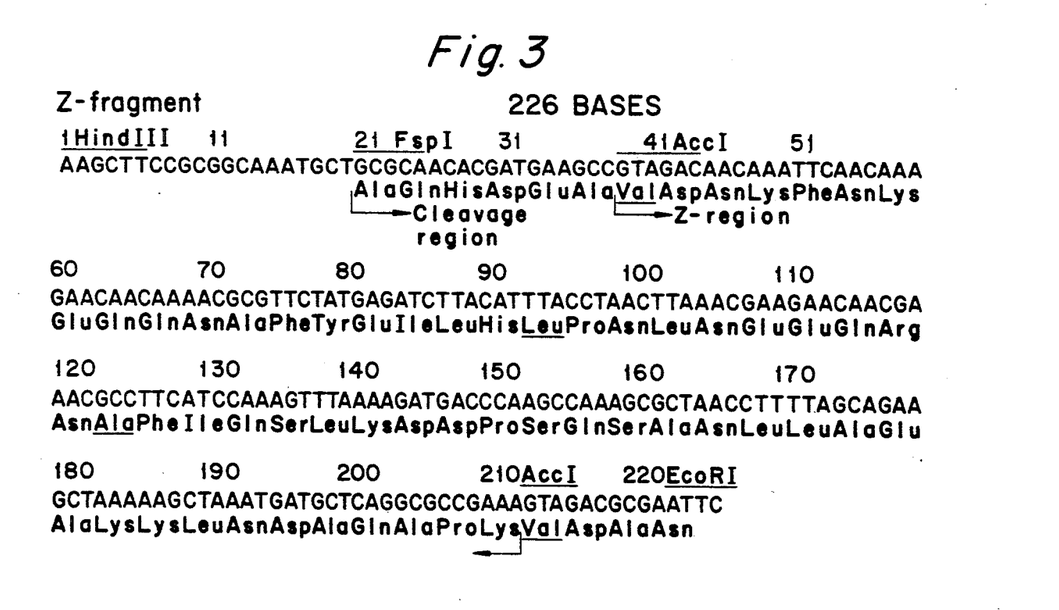
FIG. 3 shows the nucleotide sequence of the sense strand of the synthezised Z-fragment. The cleavage region is the stretch of amino acids needed for processing of the signal sequence. The Z-region is the part of the Z-fragment coding for the IgG binding domain. The amino acid changes are underlined. The restriction enzyme recognition sequences for sites used in the Examples are shown.
Figure 5:
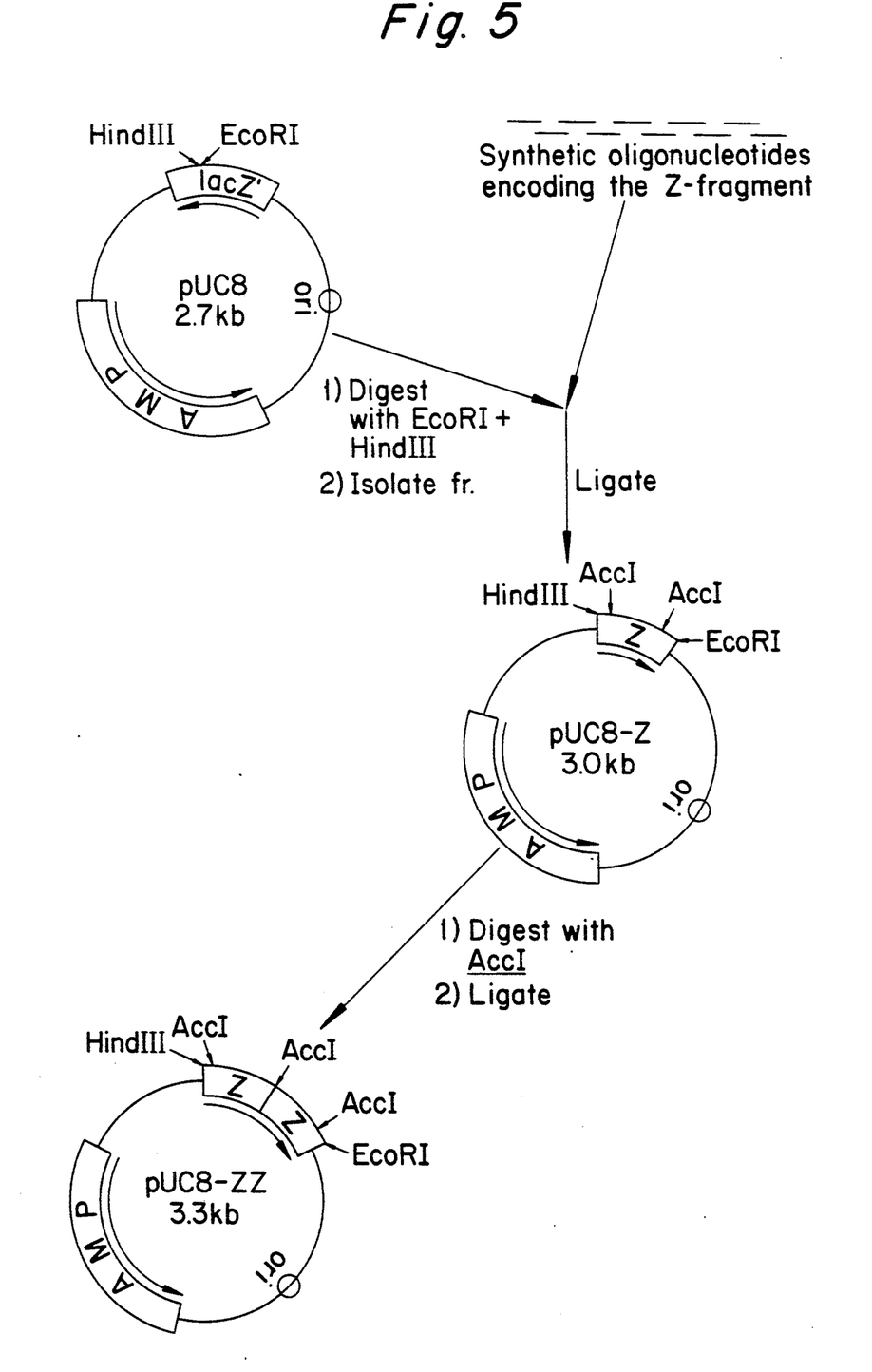
FIG. 5 shows the strategy described in Examples section V. The synthetic oligomers were cloned in M13 mp 18 (not shown in the figure) prior to the cloning of the Z-fragment (from Hind III to Eco RI) into pUC8. By digesting pUC8-Z with AccI the Z-region is cleaved out and by religation followed by transformation the pUC8-ZZ plasmid vector could be isolated. AMP is the gene coding for the β-lactamase gene, ori is the origin of replication for E.coli, lac Z' is the gene coding for β-galactosidase alpha fragment and Z is the synthetic fragment.

The vector has the synthetic Z-fragment (FIG. 3) directly after the signal sequence of protein A.

The construction was confirmed by DNA sequencing.

IV Expression of pASZ2

Expression of pASZ2 in E. coli HB101.

The strain was inoculated to 15 ml TSB and after incubation in a shake flask for 12 h the cell suspension was centrifuged.

The cells were washed once in TE (5 ml) and was further resuspended in 5 ml TSB followed by sonication for 3$\times$30 s (MSE sonicator, microtip, power 6). After sonication the mixture was centrifuged 10,000 xg for 10 minutes.

The growth media and the extract from the cell sonication was assayed for protein A using the method described in Routine Methods. The results are shown in Table 1:

TABLE 1

| Plasmid | Filamentous growth | Expression level (mg/l) | % extra-cellular |
| --- | --- | --- | --- |
| pASZ2 | + | 3.6 | 72 |

These results show that the fragment is IgG binding.

V Construction of Dimeric Z Fragment

The single stranded DNA from M13-Z was annealed to the sequencing primer followed by treatment with Klenow and dNTPs.

In this way double stranded DNA obtained. The reaction mixture was digested with HindIII and EcoRI and the Z fragment was isolated from a Low Gel Temperature Agarose gel electrophoresis. Separately the plasmid pUC 8 was digested with EcoRI and HindIII and the large fragment was isolated from Low Gel Temperature Agarose gel electrophoresis. The two isolated gel fragments were heated to 65° C. and 2 µl of each melted fragment were ligated in 50 µl ligation buffer and 2.5 units DNA ligase at 15° C. overnight. The DNA thus obtained was used to transform $E.$ $coli$ strain JM83 as above, and plasmid DNA from two transformants was isolated and proved to contain the Z fragment. The pUC 8-Z was digested with restriction enzyme AccI. After religation of the digestion mixture a new transformation of JM83 was made, followed by plasmid isolation from 12 transformants. Digestion with HindIII and EcoRI and analysis on agarose gel confirmed that 2 transformants carried the pUC 8 with an insert of two Z fragments (pUC 8-ZZ).

VI Construction of the Expression Vector pZZ-IGF-I

Figure 6:
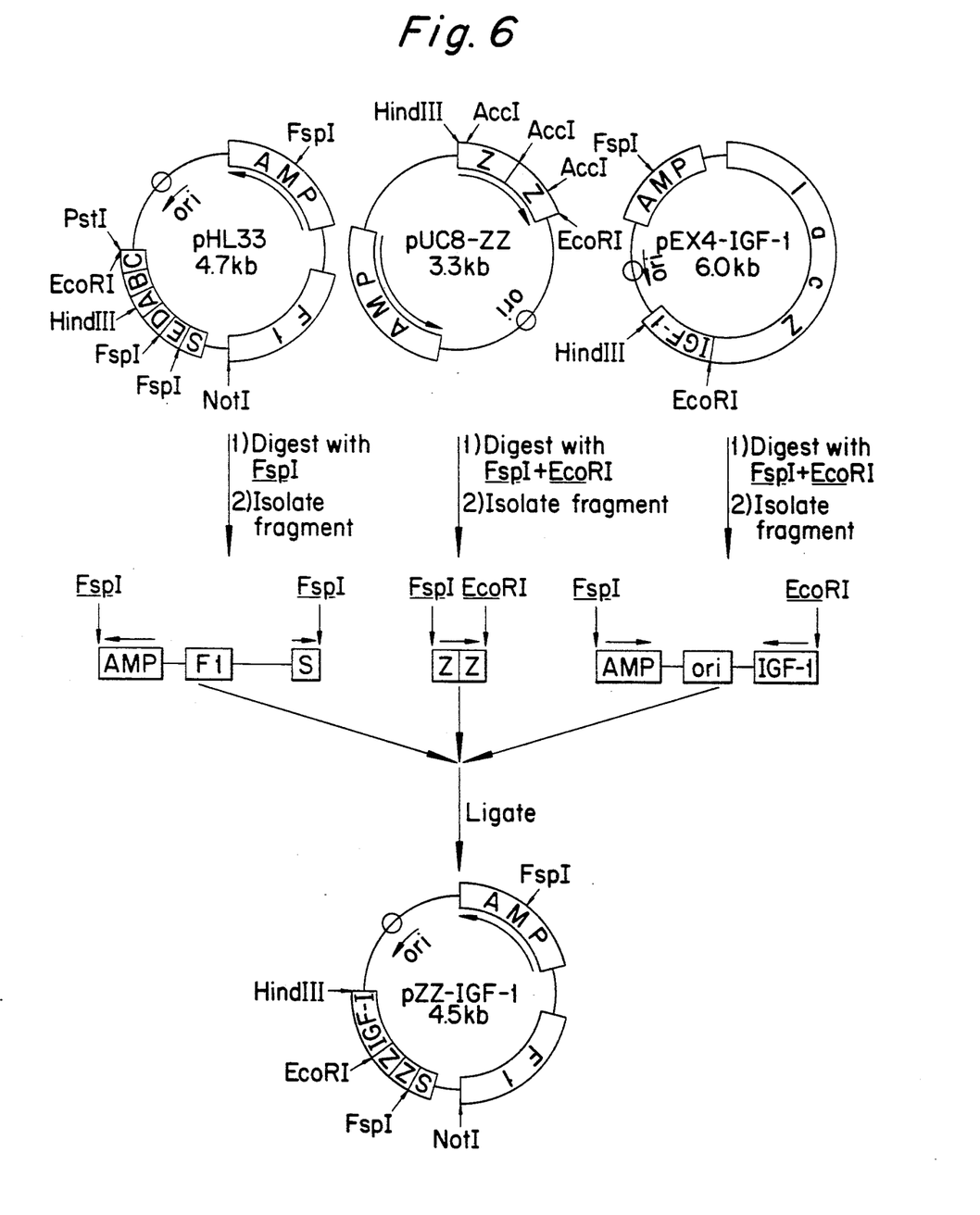
FIG. 6 shows the cloning strategy described in Examples section VI. AMP is the gene coding for β-lactamase, S is the signal sequence, A–E are the IgG binding domains of protein A, ori is the origin of replication, Z is the synthetic fragment, IGF-I is the gene for IGF-I, F1 is the origin of replication from phage f1 and lacZ is the gene for β-galactosidase.

The construction of pZZ-IGF-I was made in the following way (FIG. 6):

A. pUC18-ZZ was digested with FspI and EcoRI and the smallest fragment was isolated on LGT agarose.

B. The plasmid vector pHL33 was digested with FspI. The largest fragment (2273 bp) was isolated on LGT agarose.

C. The plasmid pEX4-IGF-I was digested with FspI and EcoRI. The small fragment spanning over the IGF-I gene into the AMP gene was isolated.

The three fragments from A, B and C were ligated together as described in Routing Methods and the ligation mixture was transformed into $E.$ $coli$ JM83.

Transformant selection was conducted using a LB agar medium containing 70 µg/ml of ampicillin. Isolation of the plasmid DNA and analysis with restriction enzymes confirmed that the transformants carried the plasmid pZZ-IGF-I.

VII Growth of $E.$ $coli$ JM83 Containing pZZ-IGF-I and Purification of IGF-I 4 l of growth medium LB supplemented with 0.2% glucose, 0.01M MgSO$_4$ and Ampicillin (100 µg/ml) was inoculated with $E.$ $coli$ JM83/pZZ-IGF-I. The cells were grown in shake flasks for 20 h at 37° C. in 2 l flasks with 500 ml broth in each flask. The cells were spun down and kept at −20° C. for 3 days. To the frozen pellet (32 g net weight) 128 ml 10 mM tris HCl pH 8.0 solution was added and the cell suspension was gently mixed for 2 h at +4° C. The cells were spun down by centrifugation and the supernatant was recovered for affinity chromatography. The supernatant was recentrifuged before application to an IgG sepharose column with 150 mM NaCl 50 mM tris HCl pH 7.5 (hereinafter TS).

Figure 8:
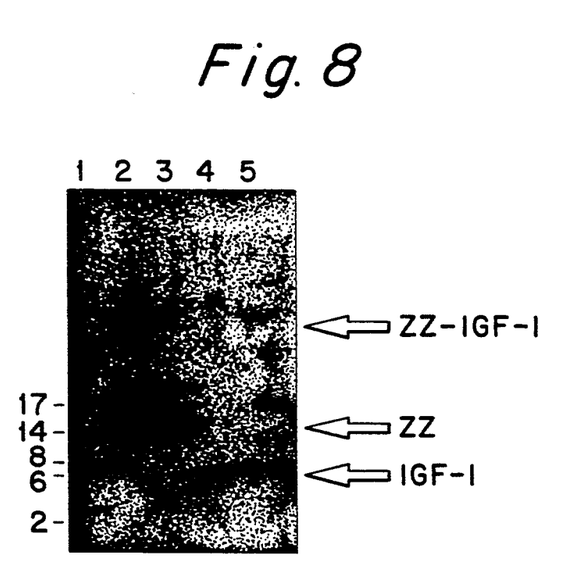
FIG. 8 shows the strategy of the process to purify IGF-I using the method of unique Asn-Gly cleavage, as described in Examples section VII.
Figure 9:
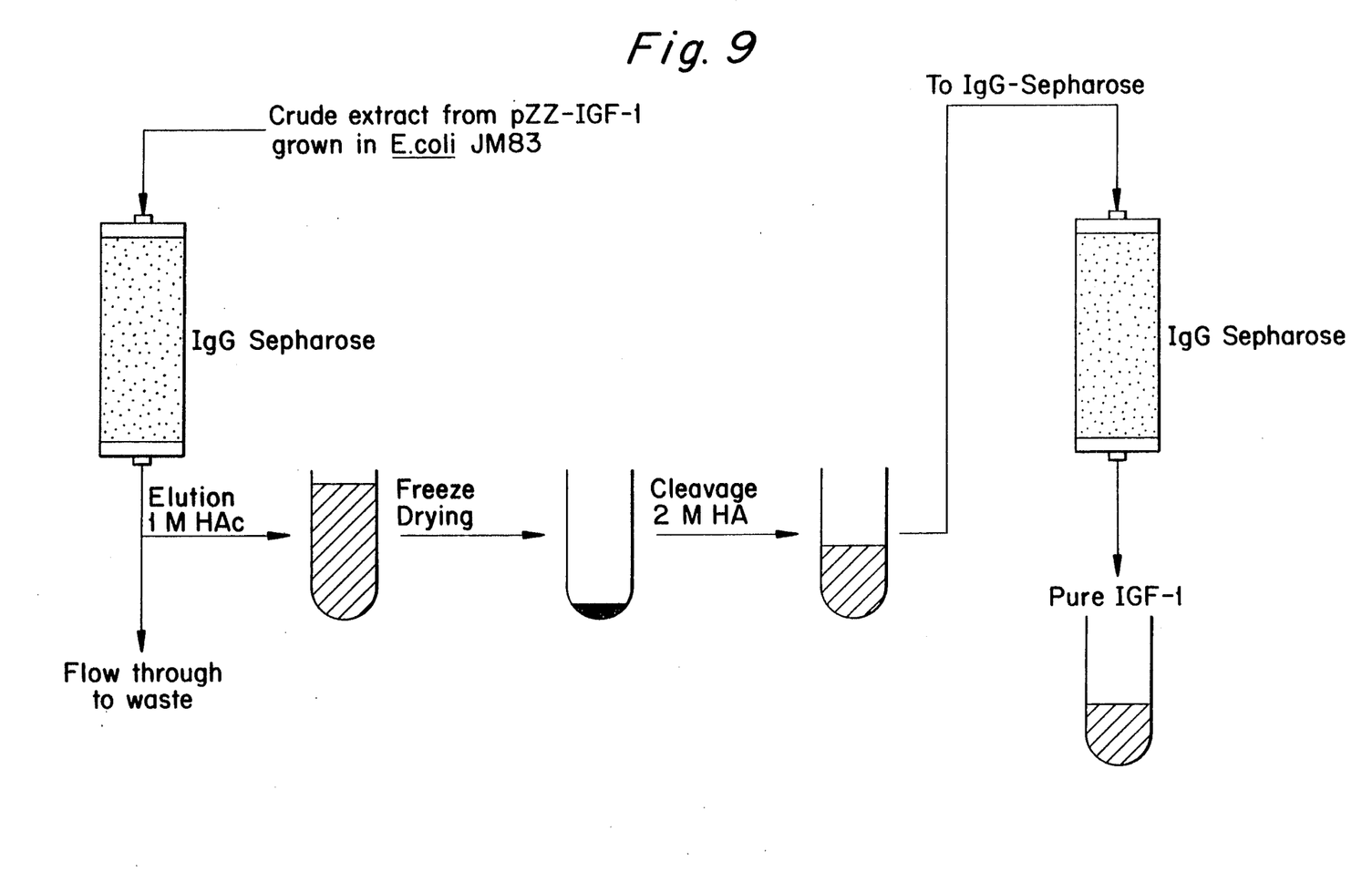
FIG. 9 shows the SDS gel electrophoresis of the proteins corresponding to the different steps in the process described in Examples section VII. Lane 1 shows size markers in Kilo Daltons, lane 2 shows the hydrid protein after IgG affinity purification, lane 3 shows the result of hydroxylamine cleavage, lane 4 shows the flow through of an IgG sepharose gel of hydroxylamine digested hybridprotein and lane 5 is pure IGF-I (marker). The bands corresponding to ZZ-IGF-I, ZZ and IGF-I are shown by arrows.

The supernatant was passed through the column at a speed of 12 ml/h and the amount of IgG binding material was analyzed before and after it was run through the column. The bound material was washed with TS supplemented with 0.05% Triton X-100 and then TS and finally with 0.05M ammonium acetate before elution with 1M acetic acid pH adjusted to 2.8 with ammonium acetate. The 2 ml fractions were assayed for protein A content and the fractions were pooled and freeze dried. The hybrid protein was cleaved with hydroxyl amine as described by Bornstein, et al, Methods Enzymol., 47, 132 (1977). The dry material was dissolved in 2M hydroxylamine adjusted to pH 9 with lithium chloride and 0.2M Tris base. The cleavage was performed at 45° C. for 4 h. The cleavage reaction was stopped by lowering the pH to 7.0 with acetic acid and the material was desalted on a PD-10 column saturated with TS. The desalted fraction of 3.5 ml was passed through a 1 ml IgG-sepharose column to separate IGF-I from the ZZ polypeptide. This material was then desalted on a PD-10 column saturated with 0.2M acetic acid, and then freeze dried. The material was then analyzed on sodium dodecyl sulphate polyacrylamide gel electrophoresis. This process is shown in FIG. 8, and the SDS-polyacrylamide gel is shown in FIG. 9. The nucleotide sequence of the expressed fusion protein is shown in FIG. 4.

These results show that the ZZ fragment is functional in a process to purify IGF-I in respect to binding IgG to facilitate purification as well as harboring a unique Asn-Gly cleavage site to release native IGF-I and to enable the ZZ portion to bind to the IgG gel after a second passage through the gel.

Although the invention has been exemplified in regard to purification of IGF-I, it is to be noted that the invention is applicable to purification of any gene coding for a useful protein. Thus, IGF-I-purification is only one example of the usefulness of the invention and is not to be construed to limit the scope of the invention otherwise than as defined in the appended patent claims.

The Asp-Pro dipeptide constellation present in all protein A domains known to bind human IgG (FIG. 2) was designed to be changed to a Glu-Pro. This will make the normally acid labile Asp-Pro peptide bound resistant to acid treatment (like 70% Formic Acid at 42° for 12 h) making any other introduced Asp-Pro coding linker unique. This designed amino acid change (Asp to Glu) is not shown in Examples.

We claim:

1. A recombinant DNA fragment (Z) coding for an immunoglobulin G binding domain related to staphylococcal protein A, wherein the methionine codon of said fragment has been replaced by a codon of an amino acid residue other than methionine enabling expression of a methionine-free protein, wherein the codon of the first amino acid residue as defined by trysin digestion of native protein A, has been replaced by a valine codon, so as to enable polymerization of said fragment to any multiplicity to enhance the binding capacity of the translated product.

2. The fragment of claim 1, wherein the glycine codon has been replaced by an alanine codon.

3. The fragment of claim 1, wherein the codon of the first amino acid residue, as defined by trypsin digestion of native protein A, has been replaced by the valine codon to obtain the sequence GTAGAC at the nucleatide level thereby furnishing a non-palindromic Acc I site.

4. The fragment of claim 3, wherein 9 glycine codon has been replaced by an alanine codon.

5. The fragment of claim 1, wherein the Asp-Pro codons have been modified to increase the acid stability of the peptide bond of the expressed protein.

6. The fragment of claim 5, wherein the aspartic acid codon has been replaced by a glutamic acid codon.

7. A plasmid vector comprising a recombinant DNA fragment (Z) of claim 1 operatively linked to a gene which encodes a protein product.

8. A bacterial cell containing the plasmid vector according to claim 7.

9. The fragment of claim 1, wherein asparagine-methionine codons of said fragment have been replaced by histidine-leucine codons.

10. The fragment of claim 9, wherein the codon of the first amino acid residue, as defined by trypsin digestion of native protein A, has been replaced by the valine codon to obtain the sequence GTAGAC at the nucleotide level thereby furnishing a non-palindromic Acc I site.

11. The fragment of claim 9, wherein the glycine codon has been replaced by an alanine codon.

12. A recombinant DNA fragment comprising at least two recombinant DNA fragments as defined in claim 1.

13. A recombinant DNA fragment comprising the fragment of claim 12, wherein said DNA sequence is preceded by a signal sequence and said DNA sequence is followed by a nucleotide sequence coding for the amino acids:

Ala Gln His Asp Glu Ala.

14. The fragment of claim 12, wherein the number of said fragments is within the range of 2 to 15.

15. A recombinant DNA fragment comprising the sequence of the fragment of claim 14, wherein said DNA sequence is preceded by a signal sequence and said DNA sequence is followed by a nucleotide sequence coding for the amino acids:

Ala Gln His Asp Glu Ala.

16. The fragment of claim 1, wherein the codon of said amino acid residue other than methionine is leucine.

17. The fragment of claim 16, wherein the asparagine-methionine codons of said fragments have been replaced by histidine-leucine codons.

18. The fragment of claim 16, wherein the codon of the first amino acid residue, as defined by trypsin digestion of native protein A, has been replaced by the valine codon to obtain the sequence GTAGAC at the nucleotide level thereby furnishing a non-palindromic Acc I site.

19. The fragment of claim 16, wherein the glycine codon has been replaced by an alanine codon.

20. A bacterial cell harboring the recombinant DNA fragment (Z) of claim 1 operatively linked to a gene which encodes a protein product.

21. The bacterial cell according to claim 20 harboring said fragment (Z) in its chromosome.

22. The bacterial cell according to claim 20 which is Gram negative.

23. The bacterial cell according to claim 22 which is *E. coli.*

24. A recombinant DNA fragment comprising the Z-fragment of claim 1, wherein said Z-fragment is preceded by a signal sequence and said Z-fragment is followed by a nucleotide sequence coding for the amino acid sequence:

Ala Gln His Asp Glu Ala.

25. A plasmid vector comprising a recombinant DNA fragment of claim 24 operatively linked to a gene which encodes a protein product.

26. A bacterial cell containing the plasmid vector according to claim 25.

27. A bacterial cell harboring a recombinant DNA fragment comprising the recombinant DNA fragment of claim 26 operatively linked to a gene which encodes a protein product.

28. A bacterial cell according to claim 27 harbouring said fragment in its chromosome.

29. A bacterial cell according to claim 27, which is Gram negative.

30. A bacterial cell according to claim 29, which is an *E. coli.*

* * * * *